US010166013B2

United States Patent
(12) United States Patent
Nguyen et al.

(10) Patent No.: US 10,166,013 B2
(45) Date of Patent: Jan. 1, 2019

(54) FLEXIBLE MEMBER FOR ANGLED SYSTEM

(71) Applicant: Medtronic Xomed, Inc., Jacksonville, FL (US)

(72) Inventors: Thoai Nguyen, Jacksonville, FL (US); Phillip Berman, Jacksonville, FL (US); Louis M. Shadeck, Dunnellon, FL (US); Luis A. Brignoni, Jacksonville, FL (US); Nawaz Maditheti, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 381 days.

(21) Appl. No.: 14/927,933

(22) Filed: Oct. 30, 2015

(65) Prior Publication Data

US 2017/0119363 A1 May 4, 2017

(51) Int. Cl.

*A61B 17/32* (2006.01)
*A61B 17/00* (2006.01)
(Continued)

(52) U.S. Cl.

CPC ........ *A61B 17/00234* (2013.01); *A61B 17/32* (2013.01); *A61B 17/32002* (2013.01); *A61B 17/320016* (2013.01); *A61M 25/0054* (2013.01); *A61M 25/0138* (2013.01); *A61B 2017/00305* (2013.01); *A61B 2017/00955* (2013.01); *A61B 2017/320032* (2013.01); *A61B 2217/005* (2013.01); *A61B 2217/007* (2013.01)

(58) Field of Classification Search

CPC .............. A61B 17/00234; A61B 17/32; A61B 17/320016; A61B 17/32002; A61B 17/3205; A61B 2017/00292; A61B 2017/003; A61B 2017/00305; A61B 2017/00309; A61B 2017/00314; A61B 2017/00336; A61B 2017/320024; A61B 2017/320032; A61M 25/0013; A61M 25/0054

See application file for complete search history.

(56) References Cited

U.S. PATENT DOCUMENTS 5,152,744 A * 10/1992 Krause ............ A61B 17/32002 604/22
5,254,130 A * 10/1993 Poncet .................. A61B 17/29 600/564

(Continued)

FOREIGN PATENT DOCUMENTS

EP 0445918 A1 9/1991

OTHER PUBLICATIONS

International Search Report and Written Opinion dated Jan. 20, 2017 for International Application No. PCT/US2016/058685 claiming the benefit of U.S. Appl. No. 14/927,933, filed Oct. 30, 2015.

(Continued)

*Primary Examiner* — Ryan J Severson
(74) *Attorney, Agent, or Firm* — Harness Dickey

(57) ABSTRACT

Disclosed is an instrument that may an interior tube and an external tube. The exterior tube may be fixed relative to an interior tube, where the interior tube may rotate or oscillate relative to the exterior tube. Further, the two tubes may be co-bent such that an angle is formed by both of the tubes.

20 Claims, 4 Drawing Sheets

(51) Int. Cl.
*A61M 25/00* (2006.01)
*A61M 25/01* (2006.01)

(56) References Cited

U.S. PATENT DOCUMENTS 5,322,505 A * 6/1994 Krause .............. A61B 17/32002 604/24
5,411,514 A * 5/1995 Fucci .............. A61B 17/32002 606/180
5,437,630 A * 8/1995 Daniel .............. A61B 17/32002 604/22
5,510,070 A * 4/1996 Krause .............. A61B 17/32002 219/69.12
5,601,583 A * 2/1997 Donahue .............. A61B 17/32002 604/22
5,620,447 A * 4/1997 Smith .............. A61B 17/32002 604/22
5,704,534 A * 1/1998 Huitema .............. A61B 17/07207 227/175.1
5,707,350 A * 1/1998 Krause .............. A61B 17/32002 604/22
5,833,692 A * 11/1998 Cesarini .............. A61B 17/32002 606/170
6,312,438 B1 * 11/2001 Adams .............. A61B 17/32002 606/159
RE38,018 E * 3/2003 Anctil .............. A61B 17/32002 156/293
6,533,749 B1 * 3/2003 Mitusina .............. A61B 17/32002 604/22
6,620,180 B1 * 9/2003 Bays .............. A61B 17/32002 606/171
6,656,195 B2 * 12/2003 Peters .............. A61B 17/32002 606/159
8,202,288 B2 * 6/2012 Adams .............. A61B 17/32002 606/170
8,277,474 B2 * 10/2012 Norman .............. A61B 17/32002 606/171
9,155,555 B2 * 10/2015 O'Brien, II .............. A61B 17/32002
9,198,685 B2 * 12/2015 Edwards .............. A61B 17/32002
9,381,032 B2 * 7/2016 Edwards .............. A61B 17/32002
9,402,645 B2 * 8/2016 Norman .............. A61B 17/32002
9,474,541 B2 * 10/2016 Zider .............. A61B 17/32002
2005/0277970 A1 * 12/2005 Norman .............. A61B 17/32002 606/180
2010/0087711 A1 * 4/2010 Edwards .............. A61B 17/32002 600/139
2013/0012972 A1 * 1/2013 Norman .............. A61B 17/32002 606/170
2013/0053830 A1 2/2013 Edwards et al.
2013/0197552 A1 * 8/2013 O'Brien, II .............. A61B 17/32002 606/170
2016/0022301 A1 * 1/2016 O'Brien, II .............. A61B 17/32002 606/171
2016/0045215 A1 * 2/2016 Edwards .............. A61B 17/32002 606/170
2016/0302823 A1 * 10/2016 Nguyen .............. A61B 17/32075
2016/0345997 A1 * 12/2016 Nguyen .............. A61B 17/3205
2017/0119363 A1 * 5/2017 Nguyen .............. A61B 17/00234

OTHER PUBLICATIONS

International Preliminary Report on Patentability dated May 11, 2018 in corresponding International Application No. PCT/US2016/058685.

* cited by examiner 30
32
34
40
16
10
22
20
50
54
4
4
1A
1A
24a
24b
50
60
53
54

16
22a
22b
50

60
24b
54
10
20
24a
A

FLEXIBLE MEMBER FOR ANGLED SYSTEM

FIELD

The subject disclosure relates to a flexible tube, and particularly to a tube that is configured to be bent to a selected position for a procedure.

BACKGROUND

This section provides background information related to the present disclosure which is not necessarily prior art.

An instrument may be used to perform a procedure on a subject. The subject may include animate and inanimate objects. In various examples, an instrument may include a movable portion to assist in cutting or resecting tissue. The tissue may include human bone or soft tissue of a subject patient.

An instrument may be desired to have a hollow interior, including a lumen. The lumen may extend from a first terminal end to a collection area, such as in a collection container. Suction may be provided to draw material through a lumen and an irrigation liquid may be provided and directed through a lumen. It may be desired, however, to separate, with a liquid seal, a lumen that may be substantially coaxial with the suction lumen, even if the two lumens are curved over a portion of their length.

SUMMARY

This section provides a general summary of the disclosure, and is not a comprehensive disclosure of its full scope or all of its features.

An instrument can include an interior portion and an exterior portion, such as an interior tube and an external tube. In various embodiments, the exterior tube may be fixed relative to the interior tube, where the interior tube may rotate or oscillate relative to the exterior tube. Both the interior tube and exterior tube may be coupled to a handle or motor portion, such as the exterior tube being fixed and the interior tube being moved by a motor. Further, the two tubes may be co-bent such that an angle is formed by both of the tubes relative to the handle.

Further, in various embodiments the inner tube may be formed of several pieces. The inner tube may, however, remain substantially liquid and gas-sealed between an interior wall and an exterior wall of the tube. The tube assembly may then be positioned to allow for excision of tissue, such as a tumor or other tissue (including both hard and soft tissue). Various positions may include ear, nose, and throat (ENT) procedures or other small diameter procedures. Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figures 1, 1A:
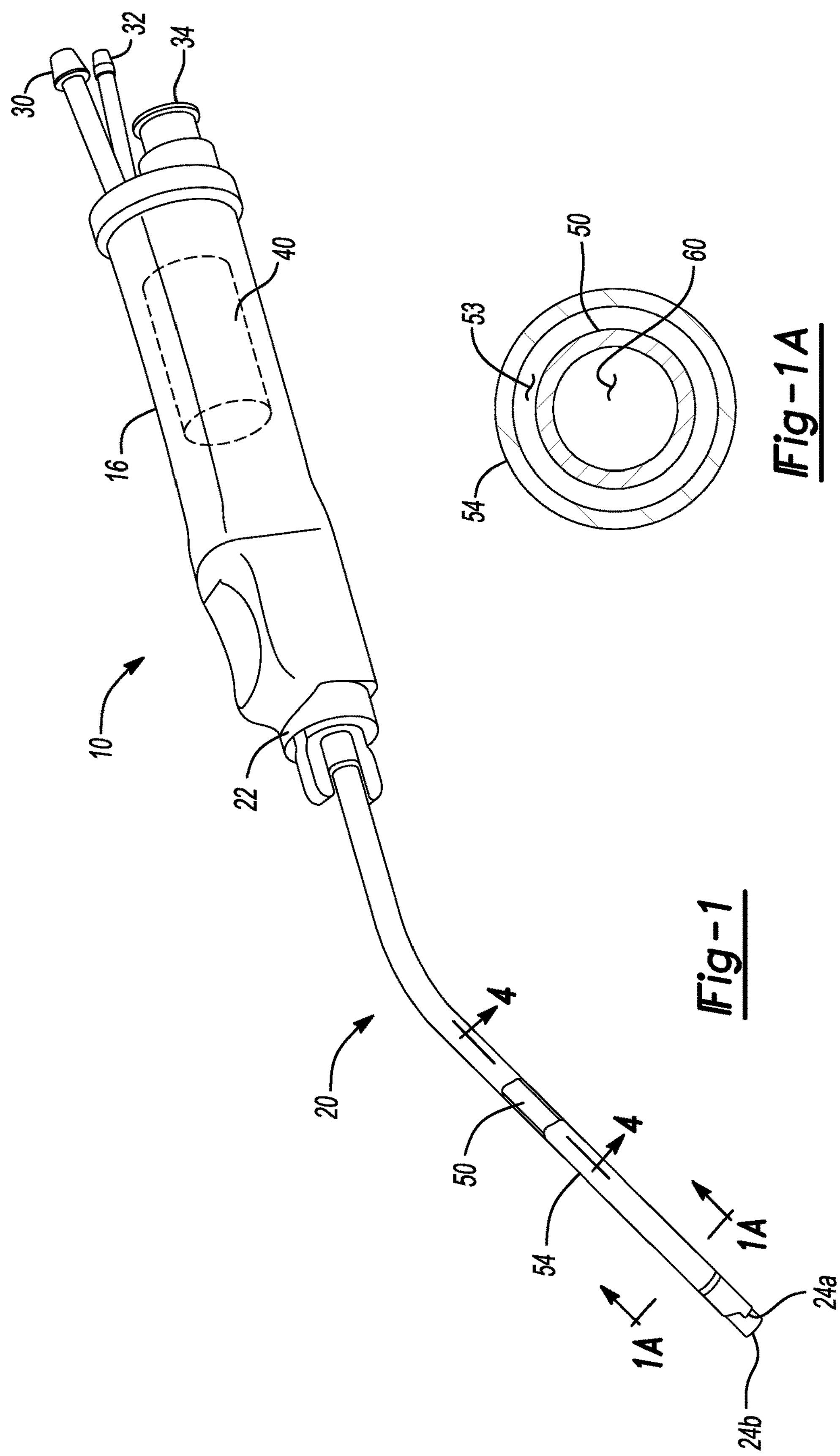
FIG. 1 is an assembled view of an instrument including a bent tube extension.
FIG. 1A is a cross-sectional view of the bent tube taken along line 1A-1A in FIG. 1.
Figure 2:
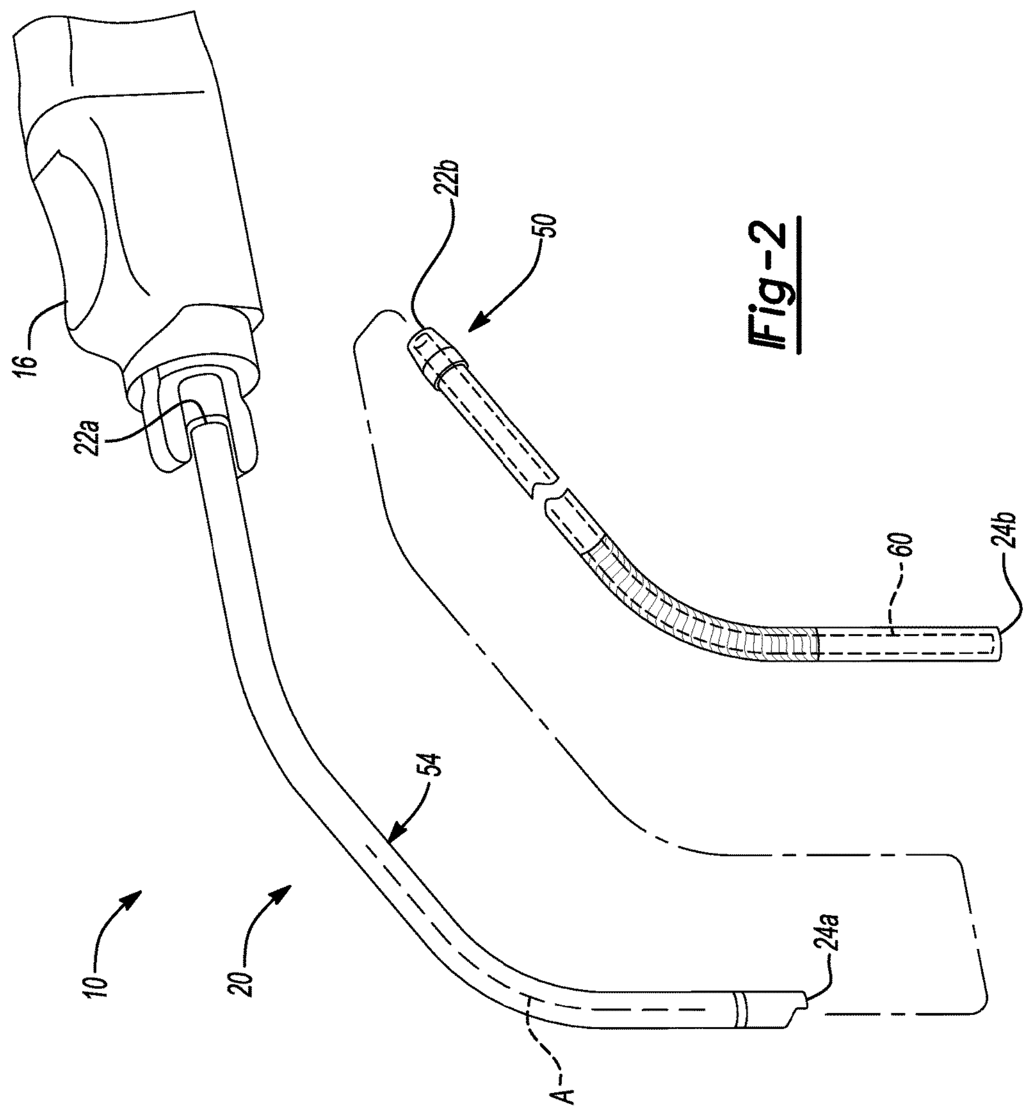
FIG. 2 is an exploded view of the instrument assembly of FIG. 1.

With reference to FIGS. 1 and 2, an instrument assembly 10 is illustrated. The instrument assembly 10 can include a handle or operating portion 16 and an tube or operating assembly 20. The tube assembly 20 extends from the handle 16 at a first proximal end 22 to a second distal working end 24. Both of the ends 22, 24 may be terminal ends. The handle 16 may include various connections including a suction connection 30, an irrigation connection 32, and a power connection 34. The power connection 34 may be an appropriate power connection such as a pneumatic power, electrical power, or the like to power a motor assembly 40 that may be positioned within the handle 16. The motor 40, therefore, can be an appropriately powered motor, such as an electrically powered and pneumatically powered motor.

The motor 40 may be operably interconnected with an inner tube 50, such as at a first end 22*b* of the inner tube 22 at or near the first end 22 of the tube assembly 20. The tube assembly 20 may further include an exterior tube 54. Each of the tubes 50, 54 may extend from the first terminal end 22 to the second terminal end 24. However, according to various embodiments, the external tube 54 may be fixed to the handle 16 while the inner tube 50 may be powered by the motor 40 to rotate and/or oscillate relative to, such as within, the outer tube 54. Therefore, the inner tube 50 may extend a distance greater than a distance of the outer tube 54. For example, the outer tube 54 may engage the handle 16 while the inner tube 50 extends to engage the motor 40 and extends beyond a first distal terminal end 24*a* of the outer tube 54 to a second terminal end 24*b*.

The tube assembly 20 may include a bend or angled region A. The angle of the angled region A may be any appropriate selected angle and may include a radius rather than a discrete or sharp angle from the first end 22 to the second end of the tube assembly 20. The angle may be formed by bending the outer tube 54 to maintain the inner tube 50 at the angle A. Thus, the outer tube 54 may be malleable so that it may be bent without collapsing. The inner tube 54, as discussed further herein, may be flexible or at least flexible at the bend region and will also not collapse when bent. The outer tube 54 may be bent to maintain a shape while the inner tube 50 may be flexible and would not maintain a bent shape if not for the outer tube 50.

The angle A may assist in defining or forming the tube assembly 20 to assist in performing various procedures such as resection of tissue in various nasal or sinus cavities or for performing other procedures. As discussed further herein, the inner tube 50 may rotate or oscillate to perform a resection or removal of selected bone tissue. As further discussed herein, the inner tube 50 may include a lumen 60 such that a material resected with the distal end 24*b* of the inner tube 50 may be suctioned through the lumen 60 with a suction source provided through the suction connection 30. The lumen 60, therefore, may form a sealed liquid path through the inner tube 50.

The outer tube 54 may also have a lumen in which the inner tube 50 is placed. With reference to FIG. 1A, a cross-section taken along lines 1A-1A of FIG. 1, a passage 53 between the inner tube 50 and the outer tube 54 forms a second liquid flow path. As discussed herein, the liquid flow path within the lumen 60 may be sealed from the liquid flow path through the passage 53. The passage 53 can allow for irrigation of an area near the working end 24*b* of the inner tube 50. For example, a saline or other fluid can be passed through the irrigation port 32 to irrigate a portion of the working area during a procedure. The seal between the two passages 60, 53 may be maintained during movement of the inner tube 50 relative to the outer tube 54.

Figure 3:
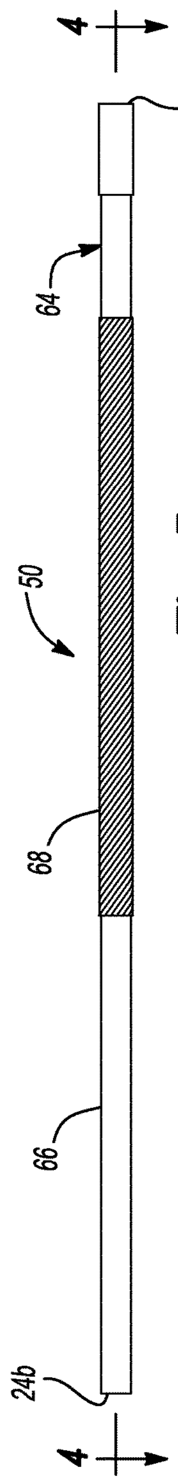
FIG. 3 is an assembled view of an internal tube of the assembly of FIG. 1.

With continuing reference to FIG. 2 and additional reference to FIG. 3, the inner tube 50 is illustrated. The inner tube 50 may include various regions or portions including a first proximal rigid region or portion 64, a distal rigid region or portion 66, and an intermediate flexible region or portion 68. As discussed further herein, the intermediate flexible region 68 can allow the inner tube 50 to be bent in a selected manner, such as in the bent region A. However, the flexible region 68 can maintain a seal between the rigid portions 64, 66 and transfer torque from the proximal rigid portion 64 to the distal rigid portion 66.

The rigid portions 64 and 66 may be formed out of selected materials, such as stainless steels, titanium or titanium alloys, or other selected materials. In various embodiments, the distal tip 24*b* of the inner tube 50 may include a sharp or cutting edge, which may be a straight sharp edge or serrated sharp edge, for performing a procedure. Accordingly, torque produced by the motor 40 can be transferred along the long axis of the inner tube 50, even if bent as illustrated in FIG. 1, to allow the inner tube 50 to rotate around the longitudinal axis of the inner tube 50 to rotate the cutting end 24*b*. The axis of the tube assembly 20, including the inner tube 50 and the outer tube 54, may be bent. Further, more than one bend or radius maybe formed. The amount of torque produced at the cutting end 24*b* may, however, be reduced from the amount produced at the proximal end 22*b*.

Figure 4:
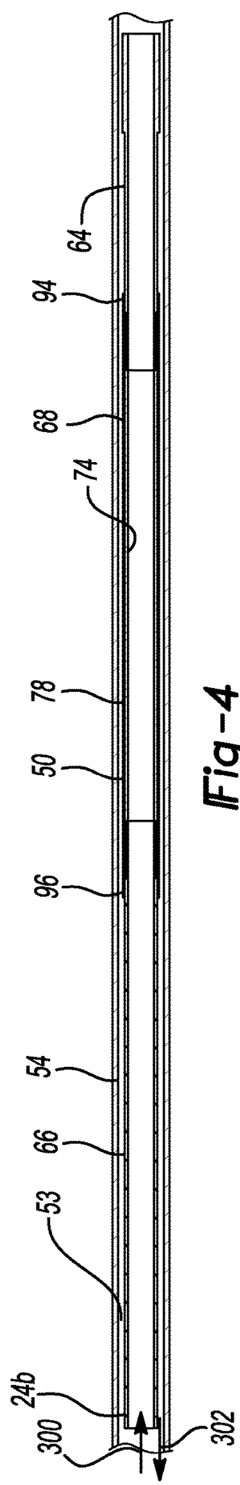
FIG. 4 is a cross-sectional view along line 4-4 of FIG. 1.

With continuing reference to FIG. 3 and additional reference to FIG. 4, the inner tube 50, including the proximal rigid portion 64, the distal rigid portion 66, and the flexible intermediate portion 68 can extend a selected distance between the two ends 22*b* and 24*b* such as about 5 inches to about 6 inches. It is understood, however, that the inner tube 50 can be provided in a selected distance or length for selected procedures.

The flexible intermediate region 68 can include at least two layers, such as an inner thermoplastic tubing portion 74 and an outer mesh or wire portion 78. The inner tube portion 74 and the outer mesh portion 78 may be interconnected with the rigid portions 64 and 66. The intermediate portion 68 allows for a transfer of torque between the proximal rigid portion 64 and the distal rigid portion 66, as discussed further herein, even across the angled portion A.

Figure 5:
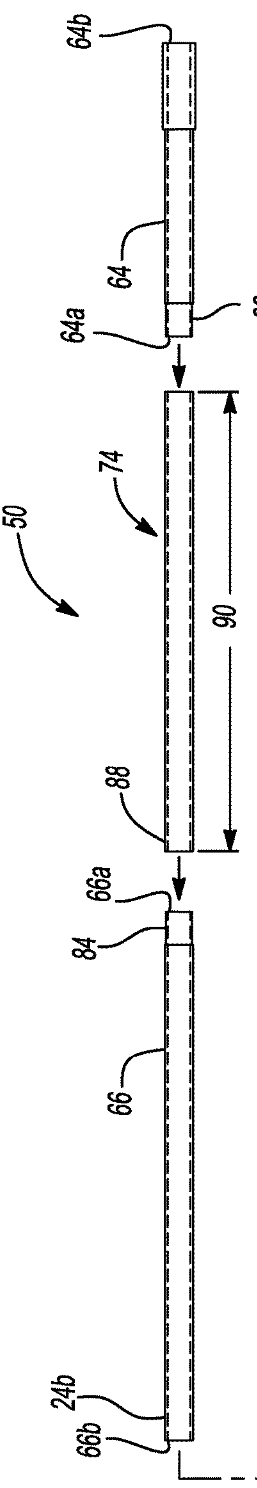
FIG. 5 is an exploded view of the tube assembly of FIG. 3.

With continuing reference to FIGS. 3 and 4 and additional reference to FIG. 5, the inner tube 50 may be formed by interconnecting the two rigid portions 64 and 66 with the intermediate tube 74. The intermediate tube 74 may be a selected polymer tube, such as a thermoplastic polymer. The thermoplastic polymer of the intermediate tube 74 may allow the intermediate tube 74 to be flexed or bent while maintaining a seal along the entire length of the inner tube 50. A thermoplastic tubing 74 may further be able to transfer appropriate torque to the distal end 24*b* under various operation conditions, such as low speed or low torque. Nevertheless, the outer coat 78 may allow for transfer of greater torque or force to the terminal end 24*b* from the motor 40.

The first rigid portion 64 may be provided as a first rigid member that extends between a first end 64*a* and a second end 64*b*, where the ends may be terminal ends. The second rigid portion 66 may be provided as a second rigid member that extends between a first end 66*a* and a second end 66*b*. The intermediate tube 74 may include an external diameter that is substantially equivalent to an external diameter of the first and second rigid members 64, 66. The intermediate tube 74 may further have an internal diameter that is substantially equivalent to or slightly larger than an outer diameter of a connecting portion 82 at or near the first end 64*a* of the proximal rigid member 64 and a connecting region 84 at the first end 66*a* of the second or distal rigid member 66. Therefore, the intermediate tube 74 may be pressed-fit over the connecting regions 82, 84 at respective terminal ends 86 and 88 of the intermediate tube 74. It is further understood that various bonding or coupling procedures may be provided such as laser welding, adhesives, or the like to interconnect the rigid members 64, 66 with the intermediate tube 74.

The outer coat portion 78 may then be passed over the rigid tube member 66 or rigid tube member 64 and over the intermediate tube 74. The intermediate tube 74 may include a length 90 that is less than a length 92 of the outer coat 78. Therefore, the outer coat 78 may include two end regions 94 and 96 that extend beyond the length of the intermediate tube 74 and overlap the rigid members 64 and 66.

The outer coat 78 may be bonded to the rigid members 64 and 66, according to various mechanisms, such as laser welding, adhesives, or the like. As the length 92 of the outer coat 78 is greater than the length 90 of the intermediate tube 74, the outer coat 78 may be bonded to the respective rigid members 64, 66 a distance from the connecting regions 82 and 84. Therefore, a substantially rigid torsional connection can be formed between the proximal rigid tube 64 and the distal rigid tube 66 that is separate from the intermediate tube 74.

The outer coat 78 may be formed of a material or construction that allows flexibility while being able to transfer torque. In transferring torque, the second or distal rigid member 66 may rotate when powered by the motor 40. Thus, rotation of the proximal rigid member 64 is transferred to the distal rigid member 66 though the outer coat 78.

Figure 6:
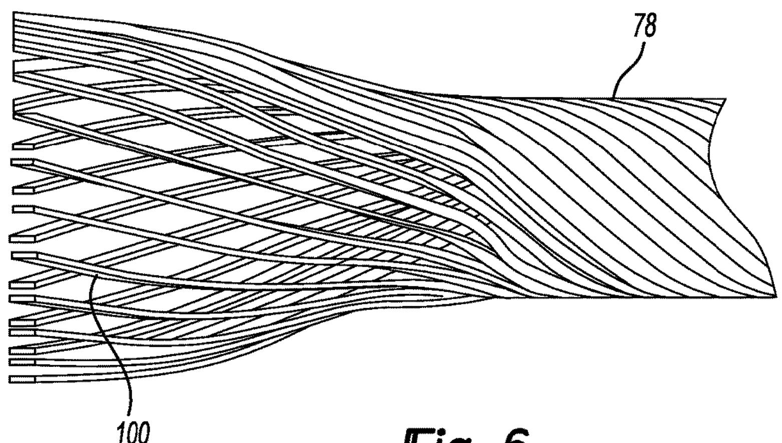
FIG. 6 is a detailed view of a portion of the inner tube.

With continuing reference to FIG. 5 and additional reference to FIG. 6, the outer coat 78 may be formed of a plurality of wires that are twisted together. It is further understood that the outer coat 78 may be formed of a plurality of wires that are woven together in a mesh form. The outer coat 78, therefore, can include a plurality of wires 100 wound or twisted. The tightness or the winding or twisting may be selected for various conditions.

At an end of the coat 78, such as the ends 94, 96, the plurality of wires may be bonded to the respective rigid members 64, 66. When bonded, the coat 78 allows for transfer of torque from the motor 40 through the proximal rigid member 64 to the distal rigid member 66. The distal rigid member 66 may then rotate and the distal terminal end 24*b* may cut or abrade a selected portion, such as tissue of a patient, according to an appropriate procedure.

The outer coat 78 may transfer torque to the cutting end with a selected efficiency. Further, the outer coat 78 may transfer bi-directional torque as the multiple wires 100 are bonded to the respective rigid members 64 and 66. The plurality of wires bonded at both ends may assist in providing appropriate bi-directional (e.g. rotating both left and right) during use. It can be selected, however, to have a two separate of the outer coats 78 where the individual wires of the two coats are twisted in opposite directions (i.e. one coat twisted to the left and another coat twisted to the right). Further, the frequency of the turns of the wire 100 and the gauge of the wire 100 may be selected to increase torque transfer and/or select the amount of flexibility.

Figure 7:
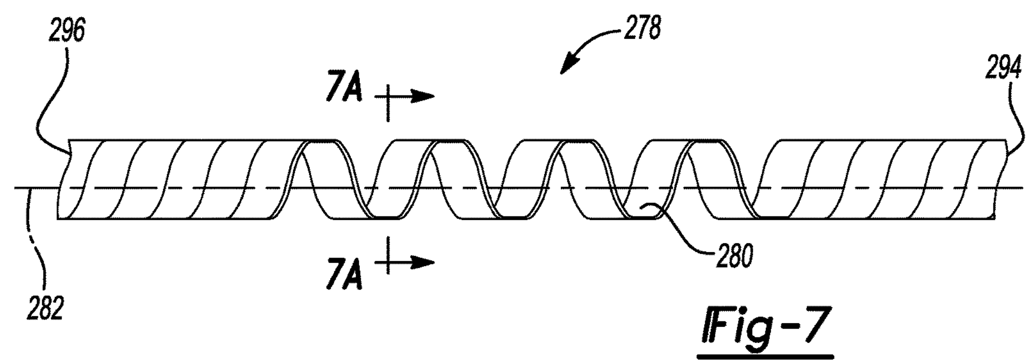
FIG. 7 is a detailed view of an alternative external coat.
Figure 7A:
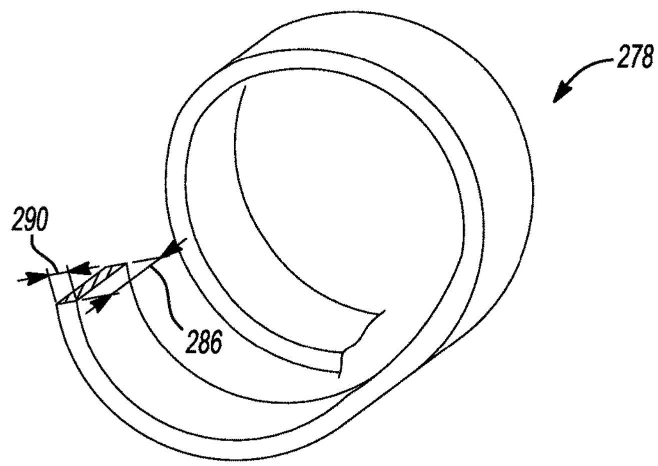
FIG. 7A is a cross-sectional view take along line 7A-7A in FIG. 7.

Turning reference to FIGS. 7 and 7A, an outer coat 278 is illustrated. The outer coat 278 can be used in place of the coat 78 in the intermediate tube portion 68. As illustrated in FIGS. 7 and 7A, a flat wire member 280 may be wound around an axis 282 to form a spiral or helix. As illustrated in FIG. 7A, the wire 280 may include a width 286 that is greater than a height 290. The width 286 may be a selected ratio such as 4:1 to 100:1 relative to the height 290. Therefore, the flat wire 280 can be wound such that the wire 280 extends from a first region 294 to a second region 296 similar to the regions at 94 and 96 of the coat 78. The regions 294 and 296 may extend beyond the thermoplastic tubing 74 and may be coupled to the rigid members 64, 66 in a manner similar to the coat 78.

The wire 280 may be wound in any appropriate frequency. For example, the coils of the wire 280 may touch one another or be spaced apart, as illustrated in FIG. 7. The tightness of the coil may be based upon a selected flexibility to be achieved in the flexible region 68 that interconnects the rigid member 64 and 66. It is understood that the coat 278 may have the wire 280 wound or twisted in a single direction, i.e. right or left. Thus, to provide torsional power for torque transfer in both a right and left direction, e.g. oscillating rotation, two of the coats 278 may be used. If two coats are used, one of the coats is twisted to the right and the other is twisted to the left. Both of the coats may be bonded together or separately to the rigid member 64, 66.

Torque may be transferred with the inner tube 50 using either of the coats 78 or 278. A single one of the coats 78 may transfer more than one of the coats 278. If both a right and left hand twisted coat 278 is interconnected between the two rigid members 64, 66, however, the amount of torque transferred may be substantially the same.

Regardless of the selected coat 78, 278 that is fixed to the rigid members 64 and 66, the inner tube 50 may be positioned within the outer tube 54 and coupled to the handle 16, as discussed above. The assembly includes the lumen 60 through the inner tube 50 which can allow suction generally in the direction of arrow 300, as illustrated in FIG. 4. Further, as discussed above, irrigation may be provided in the space, such as the annular space 53 between an outer wall of the inner tube 50 and an inner wall of the outer tube 54 to allow irrigation generally in the direction of arrow 302, as also illustrated in FIG. 4. Therefore, irrigation and suction can be provided near the working tip 24*b* of the inner tube 50 during a procedure.

In various embodiments, the inclusion of the thermoplastic tube 74 allows for maintaining a liquid and gas seal for separation between the lumen 60 and the passage 53. Therefore, during an entire procedure, irrigation and suction can be maintained even as torque is applied to the working end 24*b* for performing a procedure, such as a resection. The assembly of the outer tube 54 and the inner tube 50 to the handle 16 can be according to any appropriate mechanism, including those generally understood in the art. The inclusion of the inner tube 50, however, can allow for maintaining suction irrigation during an entire procedure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An instrument assembly, comprising:

a flexible tube, including, a first rigid member having a first lumen and a first end;

a second rigid member having a second lumen and a second end; and a flexible portion having a third end coupled to the first end of the first rigid member and a fourth end coupled to the second end of the second rigid member;

wherein the flexible portion has a third lumen;

wherein the first lumen, the second lumen, and the third lumen are configured to be coupled to form a first liquid flow path;

wherein the flexible portion is configured to transfer a working torque from the first rigid member to the second rigid member;

wherein a flexible fluid seal tube forms an inner layer of the flexible portion and a flexible reinforcing tube forms an outer layer of the flexible portion.

2. The instrument assembly of claim 1, further comprising:

an external tube having a fourth lumen;

wherein the external tube is configured to extend over the flexible tube;

wherein the external tube has an inner wall that cooperates with an external wall of the flexible tube for a second liquid flow path through the fourth lumen.

3. The instrument assembly of claim 1, further comprising:

a motor coupled to the flexible tube to provide a torque on the first rigid member.

4. An instrument assembly, comprising:

a flexible tube, including, a first rigid member having a first lumen and a first end;

a second rigid member having a second lumen and a second end; and a flexible portion having a third end coupled to the first end of the first rigid member and a fourth end coupled to the second end of the second rigid member;

wherein the flexible portion has a third lumen;

wherein the first lumen, the second lumen, and the third lumen are configured to be coupled to form a first liquid flow path;

wherein the flexible portion is configured to transfer a working torque from the first rigid member to the second rigid member;

wherein the flexible portion includes:

an inner polymer tube extending a first distance from the third end coupled to the first end of the first rigid member to the fourth end coupled to the second end of the second rigid member; and an external coat formed of a plurality of wires twisted around the inner polymer tube extending a second distance from a fourth end to a fifth end;

wherein the second distance is greater than the first distance;

wherein the fourth end is coupled to the first rigid member beyond the inner polymer tube and the fifth end is coupled to the second rigid member beyond the inner polymer tube.

5. The instrument assembly of claim 4, wherein each of the plurality of wires extends the second distance.

6. The instrument assembly of claim 4, wherein the inner polymer tube is a thermoplastic polymer.

7. An instrument assembly, comprising:

a flexible tube, including, a first rigid member having a first lumen and a first end;

a second rigid member having a second lumen and a second end; and a flexible portion having a third end coupled to the first end of the first rigid member and a fourth end coupled to the second end of the second rigid member;

wherein the flexible portion has a third lumen;

wherein the first lumen, the second lumen, and the third lumen are configured to be coupled to form a first liquid flow path;

wherein the flexible portion is configured to transfer a working torque from the first rigid member to the second rigid member;

wherein the flexible portion includes:

an inner polymer tube extending a first distance from the third end coupled to the first end of the first rigid member to the fourth end coupled to the second end of the second rigid member; and an external coat formed of a flat wire twisted around an axis of the inner polymer tube extending a second distance from a fourth end to a fifth end;

wherein the second distance is greater than the first distance;

wherein the fourth end is coupled to the first rigid member beyond the inner polymer tube and the fifth end is coupled to the second rigid member beyond the inner polymer tube.

8. An instrument assembly, comprising:

a flexible tube extending from a first flexible tube end to a second flexible tube end and having a flexible tube lumen that is a first sealed flow path through the flexible tube, including:

a first rigid member extending between a first end and a second end and a first lumen extending through the first and second ends, wherein the second end is the first flexible tube end, a second rigid member extending between a third end and a fourth end and a second lumen extending through the third and fourth ends, wherein the fourth end is the second flexible tube end, a first flexible portion extending between a fifth end coupled to the first end of the first rigid member and a sixth end coupled to the third end of the second rigid member, wherein the flexible portion has a third lumen, a single second flexible portion positioned over the first flexible portion including a twisted member, wherein a first twisted member end is coupled to the first rigid member separate from the first flexible portion and a second twisted member end is coupled to the second rigid member separate from the first flexible portion, wherein the first flexible portion has an entire length that extends a first distance and the second flexible portion has an entire length that extends a second distance, the second distance being greater than the first distance;

wherein the first lumen, the second lumen, and the third lumen are configured to be coupled to form the flexible tube lumen;

a malleable tube extending from a first malleable tube end to a second malleable tube end and having a malleable tube lumen that is a second sealed flow path through the malleable tube;

wherein the flexible tube is positioned within the malleable tube;

wherein the flexible portion is configured to transfer a working torque from the first rigid member to the second rigid member.

9. The instrument assembly of claim 8, wherein the first flexible tube end is configured to cut tissue.

10. The instrument assembly of claim 8, further comprising:

a motor configured to provide torque to the second flexible tube end.

11. The instrument assembly of claim 10, wherein the flexible tube is configured to rotate within the malleable tube when the motor is providing torque to the second flexible tube end.

12. The instrument assembly of claim 11, further comprising:

a vacuum source configured to provide suction through the first sealed flow path while the flexible tube is rotating;

an irrigation source configured to provide an irrigation liquid through the second sealed flow path while the flexible tube is rotating.

13. The instrument assembly of claim 11, wherein the twisted member of the second flexible member includes a plurality of wires twisted together between the first twisted member end and the second twisted member end.

14. The instrument assembly of claim 11, wherein the twisted member of the second flexible member includes a single flat wire twisted between the first twisted member end and the second twisted member end.

15. An instrument assembly, comprising:

a flexible tube, including, a first rigid member extending from a first end to a second end and defining a first lumen;

a second rigid member extending from a third end to a fourth end and defining a second lumen; and a flexible portion coupled to the second end of the first rigid member and the third end of the second rigid member and defining a third lumen, the flexible portion including, a flexible fluid sealed tube, and a flexible reinforcing tube;

wherein the flexible portion is configured to transfer a working torque from the first rigid member to the second rigid member;

wherein the flexible fluid sealed tube has an entire length that extends a first distance and the flexible reinforcing tube has an entire length that extends a second distance, the second distance being greater than the first distance.

16. The instrument assembly of claim 15, wherein the flexible fluid sealed tube is a polymer tube.

17. The instrument assembly of claim 15, wherein the flexible reinforcing tube is formed from a plurality of wires twisted to form the reinforcing tube.

18. The instrument assembly of claim 15, wherein the flexible reinforcing tube is formed from a twisted flat planar wire.

19. An instrument assembly, comprising:

a flexible tube, including, a first rigid member extending from a first end to a second end and defining a first lumen;

a second rigid member extending from a third end to a fourth end and defining a second lumen; and a flexible portion coupled to the second end of the first rigid member and the third end of the second rigid member and defining a third lumen, the flexible portion including, a flexible fluid sealed tube, and a flexible reinforcing tube;

wherein the flexible portion is configured to transfer a working torque from the first rigid member to the second rigid member;

wherein the flexible fluid seal tube forms an inner layer of the flexible portion and the flexible reinforcing tube forms an outer layer of the flexible portion.

20. The instrument assembly of claim 19, wherein the flexible fluid seal tube is a polymer tube and the flexible reinforcing tube is formed from either a plurality of wires twisted to form the reinforcing tube or a twisted flat planar wire.

* * * * *